(12) United States Patent
Amies et al.

(10) Patent No.: US 9,165,116 B2
(45) Date of Patent: *Oct. 20, 2015

(54) PATIENT DATA MINING

(71) Applicant: Cerner Health Services, Inc., Wilmington, DE (US)

(72) Inventors: Christopher Jude Amies, Pleasant Hill, CA (US); Arun Kumar Goel, Woodbridge, NJ (US); Radu Stefan Niculescu, Malvern, PA (US); Bharat R Rao, Berwyn, PA (US); Sathyakama Sandilya, Londdon (GB); Thomas R Warrick, Wayne, PA (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,870

(22) Filed: Dec. 15, 2014

(65) Prior Publication Data

US 2015/0100352 A1    Apr. 9, 2015

Related U.S. Application Data

(60) Continuation of application No. 12/488,083, filed on Jun. 19, 2009, now Pat. No. 8,949,079, which is a division of application No. 10/287,055, filed on Nov. 4, 2002, now Pat. No. 7,617,078.

(60) Provisional application No. 60/335,542, filed on Nov. 2, 2001.

(51) Int. Cl.
*G06F 7/60* (2006.01)
*G06F 17/10* (2006.01)
(Continued)

(52) U.S. Cl.
CPC ........ *G06F 19/3443* (2013.01); *G06F 17/3061* (2013.01); *G06F 19/322* (2013.01);
(Continued)

(58) Field of Classification Search
CPC ... G06F 19/322; G06F 19/324; G06F 19/325; G06F 19/326; G06F 19/327; G06F 19/328; G06F 19/34; G06F 19/3431; G06F 19/3487; G06F 17/5018; G06F 17/5036; G06F 17/5009
USPC ............................................................ 703/2
See application file for complete search history.

(56) References Cited

U.S. PATENT DOCUMENTS 8,355,924 B2   1/2013   Hertel et al.
8,560,335 B2   10/2013  Hertel et al.
(Continued)

OTHER PUBLICATIONS

Harvin, et al., "Managed Care: New Financial/Practice Strategies to Manage More Efficiently/Effectively in a Primary Care Setting," Nursing Administration Quarterly, vol. 22, Iss. 3; p. 53, 6 pgs.

*Primary Examiner* — Saif Alhija
(74) *Attorney, Agent, or Firm* — Shook, Hardy & Bacon LLP

(57) ABSTRACT

The present invention provides a data mining framework for mining high-quality structured clinical information. The data mining framework includes a data miner that mines medical information from a computerized patient record (CPR) based on domain-specific knowledge contained in a knowledge base. The data miner includes components for extracting information from the CPR, combining all available evidence in a principled fashion over time, and drawing inferences from this combination process. The mined medical information is stored in a structured CPR which can be a data warehouse.

20 Claims, 3 Drawing Sheets

(51) Int. Cl.
*G06F 19/00* (2011.01)
*G06F 17/30* (2006.01)
*G06Q 10/10* (2012.01)
*G06Q 50/22* (2012.01)
*G06Q 50/24* (2012.01)

(52) U.S. Cl.
CPC ............ *G06F19/324* (2013.01); *G06F 19/325* (2013.01); *G06F 19/327* (2013.01); *G06F 19/3431* (2013.01); *G06F 19/3437* (2013.01); *G06F 19/3481* (2013.01); *G06F 19/3487* (2013.01); *G06F 19/363* (2013.01); *G06Q 10/10* (2013.01); *G06Q 50/22* (2013.01); *G06Q 50/24* (2013.01); *G06F 19/321* (2013.01); *G06F 19/328* (2013.01); *G06F 19/345* (2013.01); *G06F 19/3406* (2013.01); *G06F 19/3418* (2013.01); *Y10S 128/92* (2013.01)

(56) References Cited

U.S. PATENT DOCUMENTS 8,589,185 B2    11/2013   Hertel et al.
8,775,208 B2    7/2014    Hertel et al.
2003/0036683 A1*   2/2003   Kehr et al. .................... 600/300

* cited by examiner

PATIENT DATA MINING

CROSS REFERENCE TO RELATED APPLICATIONS

The present application is a continuation patent application of U.S. application Ser. No. 12/488,083 filed Jun. 19, 2009, which is a divisional of application Ser. No. 10/287,055 filed Nov. 4, 2002, which claims the benefit of U.S. Provisional Application Ser. No. 60/335,542, filed on Nov. 2, 2001, all of which are incorporated by reference herein in their entirety.

FIELD OF THE INVENTION

The present invention relates to data mining, and more particularly, to systems and methods for mining high-quality structured clinical information from patient medical records.

BACKGROUND OF THE INVENTION

Health care providers accumulate vast stores of clinical information. However, efforts to mine clinical information have not proven to be successful. In general, data mining is a process to determine useful patterns or relationships in data stored in a data repository. Typically, data mining involves analyzing very large quantities of information to discover trends hidden in the data.

Clinical information maintained by health care organizations is usually unstructured. Therefore, it is difficult to mine using conventional methods. Moreover, since clinical information is collected to treat patients, as opposed, for example, for use in clinical trials, it may contain missing, incorrect, and inconsistent data. Often key outcomes and variables are simply not recorded.

While many health care providers maintain billing information in a relatively structured format, this type of information is limited by insurance company requirements. That is, billing information generally only captures information needed to process medical claims, and more importantly reflects the "billing view" of the patient, i.e., coding the bill for maximum reimbursement. As a result, billing information often contains inaccurate and missing data, from a clinical point of view. Furthermore, studies show that billing codes are incorrect in a surprisingly high fraction of patients (often 10% to 20%).

Given that mining clinical information could lead to insights that otherwise would be difficult or impossible to obtain, it would be desirable and highly advantageous to provide techniques for mining structured high-quality clinical information.

SUMMARY OF THE INVENTION

The present invention provides a data mining framework for mining high-quality structured clinical information.

In various embodiments of the present invention, systems and methods are provided for mining information from patient records. A plurality of data sources are accessed. At least some of the data sources can be unstructured. The system includes a domain knowledge base including domain-specific criteria for mining the data sources. A data miner is configured to mine the data sources using the domain-specific criteria, to create structured clinical information.

Preferably, the data miner includes an extraction component for extracting information from the data sources to create a set of probabilistic assertions, a combination component for combining the set of probabilistic assertions to create one or more unified probabilistic assertion, and an inference component for inferring patient states from the one or more unified probabilistic assertion.

The extraction component may employ domain-specific criteria to extract information from the data sources. Likewise, the combination component may use domain-specific criteria to combine the probabilistic assertions, and the inference component may use domain-specific criteria to infer patient states. The patient state is simply a collection of variables that one may care about relating to the patient, for example, conditions and diagnoses.

The extraction component may be configured to extract key phrases from free text treatment notes. Other natural language processing/natural language understanding methods may also be used instead of, or in conjunction with, phrase extraction to extract information from free text.

Data sources may include one or more of medical information, financial information, and demographic information. The medical information may include one or more of free text information, medical image information, laboratory information, prescription information, and waveform information.

Probability values may be assigned to the probabilistic assertions. The structured clinical information may include probability information relating to the stored information. The structured clinical information may be stored in a data warehouse. The structured clinical information may include corrected information, including corrected ICD-9 diagnosis codes. (The International Classification of Diseases, Ninth Revision, Clinical Modification (ICD-9-CM) is based on the World Health Organization's Ninth Revision, International Classification of Diseases (ICD-9). ICD-9-CM is the official system of assigning codes to diagnosis and procedures associated with hospital utilization in the United States. The Tenth Revision (ICD-10) has recently been released and differs from the Ninth Revision (ICD-9); it is expected to be implemented soon).

The system may be run at arbitrary intervals, periodic intervals, or in online mode. When run at intervals, the data sources are mined when the system is run. In online mode, the data sources may be continuously mined.

The domain-specific criteria for mining the data sources may include institution-specific domain knowledge. For example, this may include information about the data available at a particular hospital, document structures at a hospital, policies of a hospital, guidelines of a hospital, and any variations of a hospital.

The domain-specific criteria may also include disease-specific domain knowledge. For example, the disease-specific domain knowledge may include various factors that influence risk of a disease, disease progression information, complications information, outcomes and variables related to a disease, measurements related to a disease, and policies and guidelines established by medical bodies.

Furthermore, a repository interface may be used to access at least some of the information contained in the data source used by the data miner. This repository interface may be a configurable data interface. The configurable data interface may vary depending on which hospital is under consideration.

The data source may include structured and unstructured information. Structured information may be converted into standardized units, where appropriate. Unstructured information may include ASCII text strings, image information in DICOM (Digital Imaging and Communication in Medicine) format, and text documents partitioned based on domain knowledge.

In various embodiments of the present invention, the data miner may be run using the Internet. The created structured clinical information may also be accessed using the Internet.

In various embodiments of the present invention, the data miner may be run as a service. For example, several hospitals may participate in the service to have their patient information mined, and this information may be stored in a data warehouse maintained by the service provider. The service may be performed by a third party service provider (i.e., an entity not associated with the hospitals).

These and other aspects, features and advantages of the present invention will become apparent from the following detailed description of preferred embodiments, which is to be read in connection with the accompanying drawings.

DESCRIPTION OF PREFERRED EMBODIMENTS

To facilitate a clear understanding of the present invention, illustrative examples are provided herein which describe certain aspects of the invention. However, it is to be appreciated that these illustrations are not meant to limit the scope of the invention, and are provided herein to illustrate certain concepts associated with the invention.

It is also to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture.

Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps depicted in the accompanying figures are preferably implemented in software, the actual connections between the system components (or the process steps) may differ depending upon the manner in which the present invention is programmed.

Figure 1:
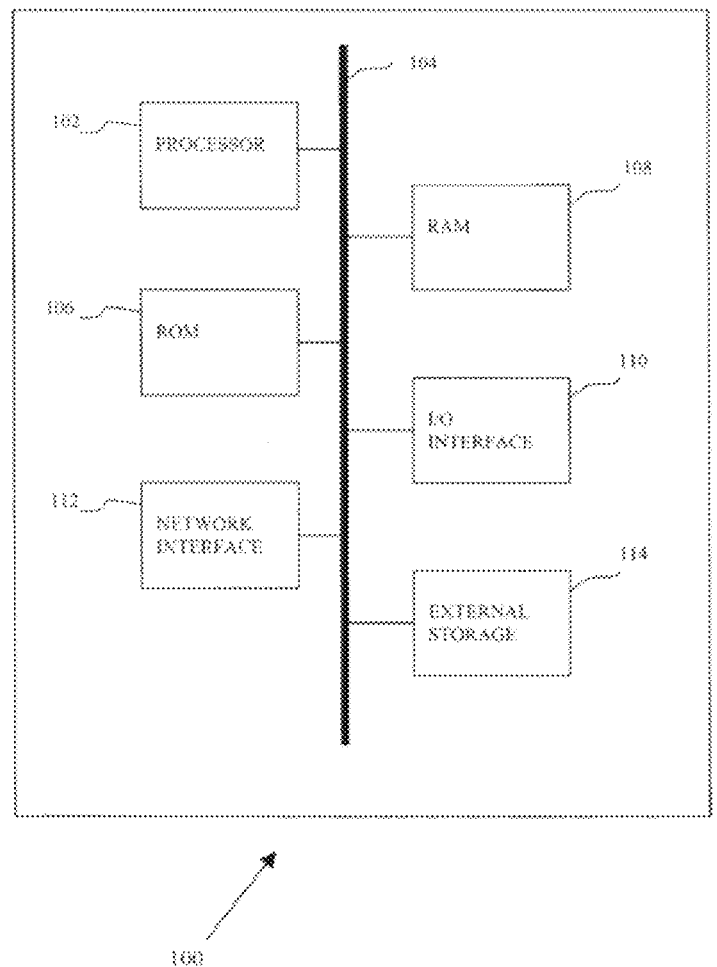
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read-only memory (ROM) 106, a random access memory (RAM) 108, an I/O interface 110, a network interface 112, and external storage 114 are operatively coupled to the system bus 104. Various peripheral devices such as, for example, a display device, a disk storage Device (e.g., a magnetic or optical disk storage device), a keyboard, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 can include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The external storage 114 may be implemented using a database management system (DBMS) managed by the processor 102 and residing on a memory such as a hard disk. However, it should be appreciated that the external storage 114 may be implemented on one or more additional computer systems. For example, the external storage 114 may include a data warehouse system residing on a separate computer system.

Those skilled in the art will appreciate that other alternative computing environments may be used without departing from the spirit and scope of the present invention.

Figure 2:
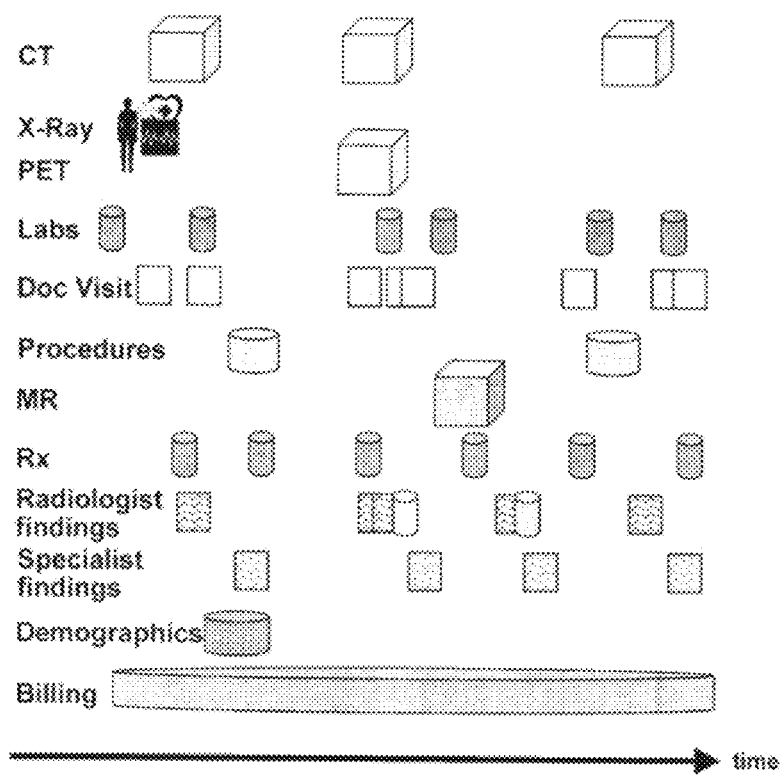
FIG. 2 shows an exemplary computerized patient record (CPR)

Increasingly, health care providers are employing automated techniques for information storage and retrieval. The use of a computerized patient record (CPR) to maintain patient information is one such example. As shown in FIG. 2, an exemplary CPR (200) includes information that is collected over the course of a patient's treatment. This information may include, for example, computed tomography (CT) images, X-ray images, laboratory test results, doctor progress notes, details about medical procedures, prescription drug information, radiological reports, other specialist reports, demographic information, and billing (financial) information.

A CPR typically includes a plurality of data sources, each of which typically reflect a different aspect of a patient's care. Structured data sources, such as financial, laboratory, and pharmacy databases, generally maintain patient information in database tables. Information may also be stored in unstructured data sources, such as, for example, free text, images, and waveforms. Often, key clinical findings are only stored within physician reports.

Figure 3:
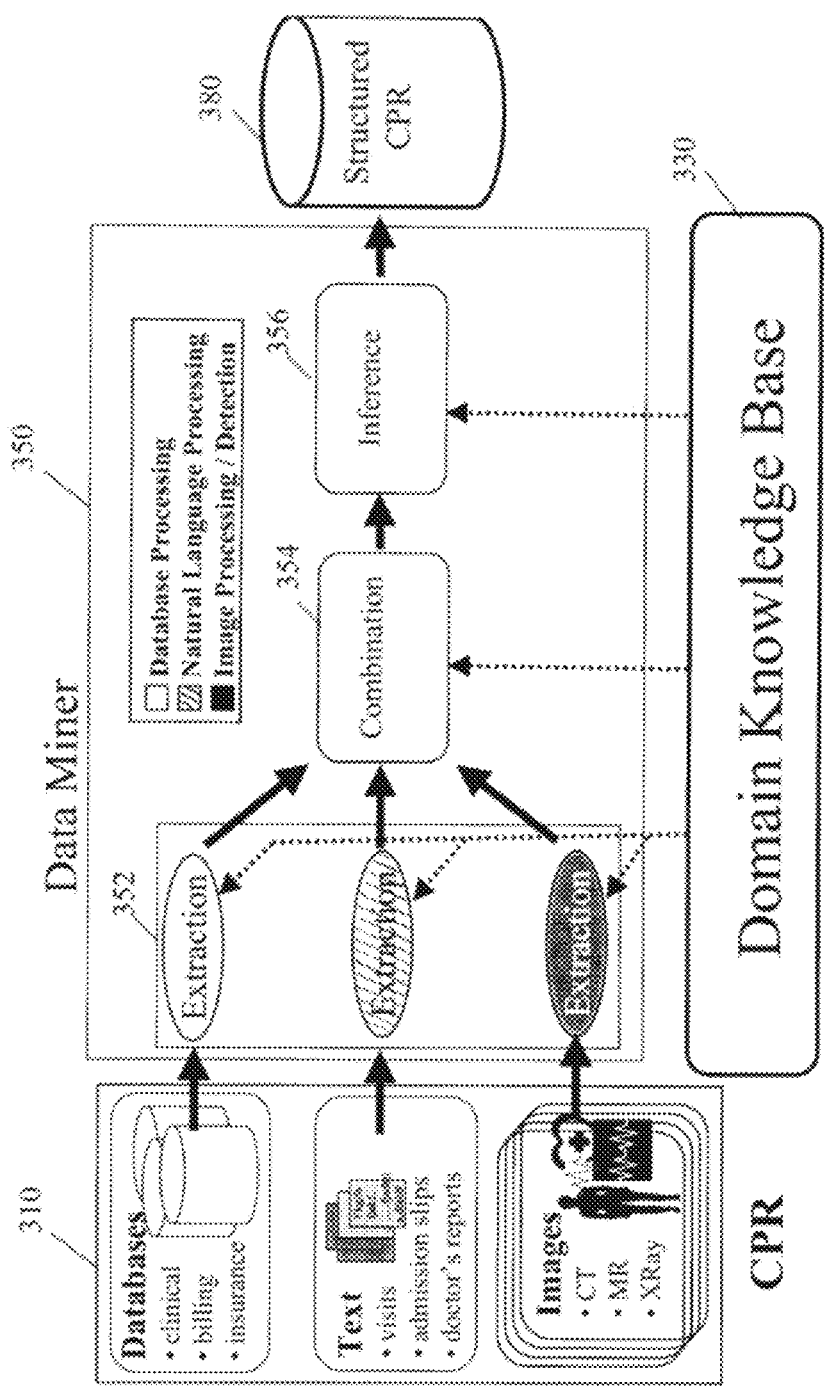
FIG. 3 shows an exemplary data mining framework for mining high-quality structured clinical information.

FIG. 3 illustrates an exemplary data mining system for mining high-quality structured clinical information. The data mining system includes a data miner (350) that mines information from a CPR (310) using domain-specific knowledge contained in a knowledge base (330). The data miner (350) includes components for extracting information from the CPR (352), combining all available evidence in a principled fashion over time (354), and drawing inferences from this combination process (356). The mined information may be stored in a structured CPR (380).

The extraction component (352) deals with gleaning small pieces of information from each data source regarding a patient, which are represented as probabilistic assertions about the patient at a particular time. These probabilistic assertions are called elements. The combination component (354) combines all the elements that refer to the same variable at the same time period to form one unified probabilistic assertion regarding that variable. These unified probabilistic assertions are called factoids. The inference component (356) deals with the combination of these factoids, at the same point in time and/or at different points in time, to produce a coherent and concise picture of the progression of the patient's state over time. This progression of the patient's state is called a state sequence.

The present invention can build an individual model of the state of a patient. The patient state is simply a collection of variables that one may care about relating to the patient. The information of interest may include a state sequence, i.e., the value of the patient state at different points in time during the patient's treatment.

Advantageously, the architecture depicted in FIG. 3 supports plug-in modules wherein the system can be easily expanded for new data sources, diseases, and hospitals. New element extraction algorithms, element combining algorithms, and inference algorithms can be used to augment or replace existing algorithms.

Each of the above components uses detailed knowledge regarding the domain of interest, such as, for example, a disease of interest. This domain knowledge base (330) can come in two forms. It can be encoded as an input to the system, or as programs that produce information that can be understood by the system. The part of the domain knowledge base (330) that is input to the present form of the system may also be learned from data.

Domain-specific knowledge for mining the data sources may include institution-specific domain knowledge. For example, this may include information about the data available at a particular hospital, document structures at a hospital, policies of a hospital, guidelines of a hospital, and any variations of a hospital.

The domain-specific knowledge may also include disease-specific domain knowledge. For example, the disease-specific domain knowledge may include various factors that influence risk of a disease, disease progression information, complications information, outcomes and variables related to a disease, measurements related to a disease, and policies and guidelines established by medical bodies.

As mentioned, the extraction component (352) takes information from the CPR (310) to produce probabilistic assertions (elements) about the patient that are relevant to an instant in time or time period. This process is carried out with the guidance of the domain knowledge that is contained in the domain knowledge base (330). The domain knowledge required for extraction is generally specific to each source.

Extraction from a text source may be carried out by phrase spotting, which requires a list of rules that specify the phrases of interest and the inferences that can be drawn therefrom. For example, if there is a statement in a doctor's note with the words "There is evidence of metastatic cancer in the liver," then, in order to infer from this sentence that the patient has cancer, a rule is needed that directs the system to look for the phrase "metastatic cancer," and, if it is found, to assert that the patient has cancer with a high degree of confidence (which, in the present embodiment, translates to generate an element with name "Cancer", value "True" and confidence 0.9).

The data sources include structured and unstructured information. Structured information may be converted into standardized units, where appropriate. Unstructured information may include ASCII text strings, image information in DICOM (Digital Imaging and Communication in Medicine) format, and text documents partitioned based on domain knowledge. Information that is likely to be incorrect or missing may be noted, so that action may be taken. For example, the mined information may include corrected information, including corrected ICD-9 diagnosis codes.

Extraction from a database source may be carried out by querying a table in the source, in which case, the domain knowledge needs to encode what information is present in which fields in the database. On the other hand, the extraction process may involve computing a complicated function of the information contained in the database, in which case, the domain knowledge may be provided in the form of a program that performs this computation whose output may be fed to the rest of the system.

Extraction from images, waveforms, etc., may be carried out by image processing or feature extraction programs that are provided to the system.

Combination includes the process of producing a unified view of each variable at a given point in time from potentially conflicting assertions from the same/different sources. In various embodiments of the present invention, this is performed using domain knowledge regarding the statistics of the variables represented by the elements ("prior probabilities").

Inference is the process of taking all the factoids that are available about a patient and producing a composite view of the patient's progress through disease states, treatment protocols, laboratory tests, etc. Essentially, a patient's current state can be influenced by a previous state and any new composite observations.

The domain knowledge required for this process may be a statistical model that describes the general pattern of the evolution of the disease of interest across the entire patient population and the relationships between the patient's disease and the variables that may be observed (lab test results, doctor's notes, etc.). A summary of the patient may be produced that is believed to be the most consistent with the information contained in the factoids, and the domain knowledge.

For instance, if observations seem to state that a cancer patient is receiving chemotherapy while he or she does not have cancerous growth, whereas the domain knowledge states that chemotherapy is given only when the patient has cancer, then the system may decide either: (1) the patient does not have cancer and is not receiving chemotherapy (that is, the observation is probably incorrect), or (2) the patient has cancer and is receiving chemotherapy (the initial inference—that the patient does not have cancer—is incorrect); depending on which of these propositions is more likely given all the other information. Actually, both (1) and (2) may be concluded, but with different probabilities.

As another example, consider the situation where a statement such as "The patient has metastatic cancer" is found in a doctor's note, and it is concluded from that statement that <cancer=True (probability=0.9)>. (Note that this is equivalent to asserting that <cancer=True (probability=0.9), cancer=unknown (probability=0.1)>).

Now, further assume that there is a base probability of cancer<cancer=True (probability=0.35), cancer=False (probability=0.65)>(e.g., 35% of patients have cancer). Then, we could combine this assertion with the base probability of cancer to obtain, for example, the assertion <cancer=True (probability=0.93), cancer=False (probability=0.07)>.

Similarly, assume conflicting evidence indicated the following:

1. <cancer=True (probability=0.9), cancer=unknown probability=0.1)>
2. <cancer=False (probability=0.7), cancer=unknown (probability=0.3)>
3. <cancer=True (probability=0.1), cancer=unknown (probability=0.9)> and
4. <cancer=False (probability=0.4), cancer=unknown (probability=0.6)>.

In this case, we might combine these elements with the base probability of cancer<cancer=True (probability=0.35), cancer=False (probability=0.65)> to conclude, for example, that <cancer=True (prob=0.67), cancer=False (prob=0.33)>.

It should be appreciated the present invention typically must access numerous data sources, and deal with missing, incorrect, and/or inconsistent information. As an example, consider that, in determining whether a patient has diabetes, the following information might have to be extracted:

(a) ICD-9 billing codes for secondary diagnoses associated with diabetes;

(b) drugs administered to the patient that are associated with the treatment of diabetes (e.g., insulin);

(c) patient's lab values that are diagnostic of diabetes (e.g., two successive blood sugar readings over 250 mg/d);

(d) doctor mentions that the patient is a diabetic in the H&P (history & physical) or discharge note (free text); and (e) patient procedures (e.g., foot exam) associated with being a diabetic.

As can be seen, there are multiple independent sources of information, observations from which can support (with varying degrees of certainty) that the patient is diabetic (or more generally has some disease/condition). Not all of them may be present, and in fact, in some cases, they may contradict each other. Probabilistic observations can be derived, with varying degrees of confidence. Then these observations (e.g., about the billing codes, the drugs, the lab tests, etc.) may be probabilistically combined to come up with a final probability of diabetes. Note that there may be information in the patient record that contradicts diabetes. For instance, the patient is has some stressful episode (e.g., an operation) and his blood sugar does not go up.

It should be appreciated that the above examples are presented for illustrative purposes only and are not meant to be limiting. The actual manner in which elements are combined depends on the particular domain under consideration as well as the needs of the users of the system. Further, it should be appreciated that while the above discussion refers to a patient-centered approach, actual implementations may be extended to handle multiple patients simultaneously. Additionally, it should be appreciated that a learning process may be incorporated into the domain knowledge base (330) for any or all of the stages (i.e., extraction, combination, inference) without departing from the spirit and scope of the present invention.

The system may be run at arbitrary intervals, periodic intervals, or in online mode. When run at intervals, the data sources are mined when the system is run. In online mode, the data sources may be continuously mined.

The data miner may be run using the Internet. The created structured clinical information may also be accessed using the Internet.

Additionally, the data miner may be run as a service. For example, several hospitals may participate in the service to have their patient information mined, and this information may be stored in a data warehouse owned by the service provider. The service may be performed by a third party service provider (i.e., an entity not associated with the hospitals).

Once the structured CPR (380) is populated with patient information, it will be in a form where it is conducive for answering several questions regarding individual patients, and about different cross-sections of patients.

The following describes REMIND (Reliable Extraction and Meaningful Inference from Non-structured Data), an innovative data mining system developed by Siemens Corporate Research (SCR), a subsidiary of Siemens Corporation. REMIND is based upon an embodiment of the present invention.

Initially, an analogy is provided that describes the spirit in which REMIND performs inferences.

A French medical student who has some knowledge about cancer is provided with cancer patient CPR's. The CPR's contain transcribed English dictations and pharmacy data. The student's task is to classify which patients have had a recurrence, and if they have, determine when it occurred. Unfortunately his English is poor, though he does know some key medical words and a few of the drug names. However, he cannot rely purely on the presence of some key words, such as metastases, in the dictation, because he knows that physicians often make negative statements ("Patient is free of evidence of metastases."). How might the student best carry out his task?

The student can collect all relevant evidence from the CPR—without trusting any single piece of evidence—and combine it to reconcile any disparities. He can use his knowledge about the treatment of cancer—for instance, on noting that a patient had a liver resection, the student can conclude that the patient (probably) previously had a recurrence.

Problem Definition

Let S be a continuous time random process taking values in $\Sigma$ that represents the state of the system. Let $T=\{t_1, t_2, \ldots, t_n\}$, where $t_i < t_{i+1}$, be the n "times of interest" when S has to be inferred. Let $S_i$ refer to the sample of S at time $t_i \in T$. Let V be the set of variables that depend upon S. Let O be set of all (probabilistic) observations for all variables, $v \in V$. Let $O_i$ be the set of all observations "assigned" to $t_i \in T$; i.e., all observations about variables, $v \in V$, that are relevant for this time-step $t_i$. Similarly, let $$seq_{MAP} = \arg\max_{seq} P[seq|O]$$

$O^j_i(v)$ be the j-th observation for variable v assigned to $t_i$. Let $seq = <S_1, S_2, \ldots, S_n>$ be a random variable in $\Sigma^n$; i.e., each realization of seq is a state sequence across T. GOAL: Estimate the most likely state sequence, $seq_{MAP}$, (the maximum a posteriori estimate of seq) given O.

REMIND extracts information, $o_i$, from every data source in a uniform format called probabilistic observations. Each $o_i$ is drawn entirely from a single piece of information in a data source (e.g., from a phrase in a sentence, or a row in a database table), and hence is assumed to be inherently undependable. The observation {"Recurrent", "12/17/01", <T=0.1, F=0.0>}, states that the Boolean variable "Recurrent" has an associated distribution over all possible values that can be taken by "Recurrent". The probabilities do not have to add up to 1.0; any remainder (here 0.9) is assigned to unknown, and is smoothed over T/F, based upon the (time-dependent) a priori distribution.

Extraction from Structured data: REMIND communicates with all databases via JDBC, Java's built-in interface to relational databases. Executing a query (e.g., retrieve drug administered) is expressed as a probabilistic observation.

Extraction from Free Text: REMIND strips document headers/footers, and tokenizes free text. Information from the token stream is extracted via phrase spotting, an easy-to-implement method from computational linguistics. Phrase spotting is about as simple as it sounds. A phrase-spotting rule is applied within a single sentence. The rule:

[metastasis & malignant] $\Rightarrow$ {"Recurrent", <T=0.5>} states that if the 2 words (actually aliases) in the rule are found in a sentence, a probabilistic observation about recurrence should be generated. REMIND also has compound rules to detect "negation" and "imprecision", which modify the probabilities in existing observations.

The primary focus of our interest is estimating what happened to the patient across T, the duration of interest. The estimation of the MAP state sequence can be done in two steps, the first of which is combination of observations at a fixed point in time and the second is the propagation of these inferences across time.

Each (smoothed) $o_i$ is in the form of an a posteriori probability of a variable given the small context that it is extracted from. All observations, $O^j_i(v)$, about a variable for a single time $t_i$ are combined into one assertion in a straightforward manner by using Bayes' theorem:

$$P[v_i | O_i^1(v_i), \ldots, O_i^k(v_i)] \propto P[v_i] \cdot \prod_{j=1}^{k} P[O_i^j(v_i) | v_i] \propto \frac{\prod_{j=1}^{k} P[v_i | O_i^j(v_i)]}{P[v_i]^{k-1}}$$

At every $t_i \epsilon T$, the relationships among $S_i$ and V are modeled using a Bayesian Network. Because the state process is modeled as being Markov and the state as being causative (directly or indirectly) of all the variables that we observe, we have the following equation:
This $$P[seq | O] \propto P[S_0] \cdot \prod_{i=2}^{n} P[S_i | S_{i-1}] \cdot \prod_{i=1}^{n} P[O_i | S_i] \propto$$

$$\prod_{i=2}^{n} \frac{P[S_i | S_{i-1}]}{P[S_i]} \cdot \prod_{i=1}^{n} P[S_i | O_i]$$

equation connects the a posteriori probability of seq (any sequence of samples of the state process across time) given all observations, to $P(S_i|O_i)$, the temporally local a posteriori probability of the state given the observations for each time instant. Essentially, we string together the temporally local Bayesian Networks by modeling each state sample, $S_i$, as the cause of the next sample, $S_{i+1}$.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for producing structured clinical information from patient records, the system comprising:
a memory configured to store a patient record having patient information including unstructured data and structured data;
a probabilistic data miner of a computer platform configured to (a) mine the structured and unstructured information for multiple pieces of data related to a variable for the patient, (b) combine the multiple pieces of data related to the variable into a value of the variable for the patient, the value being a function of the multiple pieces of data related to the variable, and (c) repeat (a) and (b) for a plurality of different variables of the same patient to find values for the variables representing the patient at a same time, the multiple pieces of data for one variable of the different variables being different than the multiple pieces of data for another one of the different variables;
wherein one or both of (a) and (b) are performed as a function of domain-specific criteria.

2. The system of claim 1 wherein the probabilistic data miner is configured to extract the multiple pieces of data as a function of the domain-specific criteria.

3. The system of claim 1 wherein the probabilistic data miner is configured to combine the multiple pieces of data for the one variable as a function of the domain-specific criteria, the domain-specific criteria comprising knowledge about a disease.

4. The system of claim 1 wherein the probabilistic data miner comprises an extraction component for extracting the multiple pieces of data and outputting a probabilistic assertion.

5. The system of claim 1 wherein the probabilistic data miner is configured to infer a patient state as a function of the values for the different variables.

6. The system of claim 5 wherein the probabilistic data miner is configured to infer the patient state as a function of probabilities, one of the probabilities assigned to each of the values.

7. The system of claim 5 wherein the inference is a function of a statistical model of a pattern of evolution of a disease across a patient population and the relationship between a patient's disease and observed variables.

8. The system of claim 1 wherein the patient information includes one or more of: medical information, financial information, demographic information or combinations thereof, the unstructured data including two or more of: the free text information, medical image information, laboratory information, prescription drug information, waveform information or combinations thereof.

9. The system of claim 1 wherein the probabilistic data miner is configured to extract key phrases from the unstructured data, the unstructured data comprising free text treatment notes, the key phrases comprising at least part of the domain-specific criteria.

10. The system of claim 1 wherein the probabilistic data miner is configured to output structured clinical information with probability information from the multiple pieces of data from the unstructured data.

11. The system of claim 1 wherein the domain-specific criteria includes institution-specific domain knowledge, disease-specific domain knowledge, or combinations thereof.

12. The system of claim 1 wherein the unstructured data includes two or more of: ASCII text strings, image information in DICOM format, text documents, or combinations thereof, partitioned based on domain knowledge.

13. The system of claim 1 wherein the probabilistic data miner is run at arbitrary intervals, periodic intervals, in an online mode, or combinations thereof.

14. The system of claim 1 wherein a repository interface is used to access at least some of the patient information used by the probabilistic data miner, wherein the repository interface is a configurable data interface, which varies depending on hospital.

15. A method for providing structured clinical information from patient records, the method comprising:
mining, by a processor, unstructured free text in a physician's note of a patient record from a healthcare provider, the mining comprising extracting evidence of a first value of a first variable;
creating, probabilistically by the processor, structured clinical data of values for respective multiple variables including the first value of the first variable, the structured clinical data for each of the multiple values created from multiple sources of mined evidence, the evidence of the first value being one of the multiple sources of mined evidence for the first variable; and providing the mining of the unstructured free text as a service to the healthcare provider;

outputting at least one of the multiple values from the structured clinical data as a function of an input question regarding a patient.

16. The method of claim 15 wherein mining comprises mining the patient record of the healthcare provider and a patient record of another healthcare provider, and wherein providing comprises providing the mining as the service to the healthcare provider and the other healthcare provider.

17. The method of claim 15 wherein providing comprises providing the service by a third party service provider.

18. The method of claim 15 wherein creating comprises:

combining a set of probabilistic assertions into one or more unified probabilistic assertions; and inferring a patient state from the one or more unified probabilistic assertions; and wherein outputting comprises communicating the patient state.

19. The method of claim 15 wherein mining comprises mining as a function of institution-specific domain knowledge of the healthcare provider.

20. The method of claim 15 wherein mining comprises mining structured and unstructured data sources for the mined evidence.

* * * * *